United States Patent
Brieden et al.

[11] Patent Number: 5,908,935
[45] Date of Patent: Jun. 1, 1999

[54] PROCESS FOR THE PREPARATION OF 1-ACYL-4-ARYLPIPERIDINES

[75] Inventors: Walter Brieden, Glis; Didier Loetscher, Leuk-Stadt; Andrew Naughton, Visp, all of Switzerland

[73] Assignee: Lonza AG, Gampel/Valais, Switzerland

[21] Appl. No.: 09/080,929

[22] Filed: May 19, 1998

Related U.S. Application Data

[62] Division of application No. 08/933,527, Sep. 18, 1997, Pat. No. 5,789,596.

[30] Foreign Application Priority Data

Sep. 18, 1996 [CH] Switzerland ............... 2280/96

[51] Int. Cl.$^6$ ................................. C07D 211/82
[52] U.S. Cl. ............................................. 546/326
[58] Field of Search ............................ 546/326

[56] References Cited

U.S. PATENT DOCUMENTS 5,374,728 12/1994 Kampmann et al. .

OTHER PUBLICATIONS

Gundersen, Lise–Lott, et al., Tetrahedron, vol. 48, No. 27, (1992), pp. 5647–5656.
Rosentreter, U., Synthesis, No. 2, (Feb. 1985), pp. 210–212.

*Primary Examiner*—Patricia L. Morris
*Attorney, Agent, or Firm*—Fisher, Christen & Sabol

[57] ABSTRACT

1-Acyl-4-arylpiperidines of the general formula:

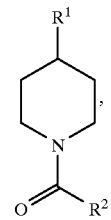

I wherein $R^1$ is an aryl group optionally substituted by one or more $C_{1-6}$-alkyl groups, $C_{1-6}$-alkoxy groups, benzyloxy groups or $C_{1-6}$-alkylthio groups and/or one or more fluorine atoms, and $R^2$ is a $C_{1-6}$-alkyl group, a $C_{1-6}$-alkoxy group, an optionally substituted aryl group, alkylaryl group or a benzyloxy group optionally substituted on the phenyl radical. The 1-acyl-4-arylpiperidines of formula I are prepared by reacting an arylmagnesium halide with a 1-acylpyridinium halide, obtainable from pyridine and an acyl halide, in the presence of a copper compound to give the corresponding 1-acyl-4-aryl-1,4-dihydropyridine, and hydrogenating the latter. The 1-acyl-4-arylpiperidines are intermediates in the synthesis of pharmaceutical active ingredients, for example, neurokinin receptor antagonists.

2 Claims, No Drawings

PROCESS FOR THE PREPARATION OF 1-ACYL-4-ARYLPIPERIDINES

This application is a division of Application Ser. No. 08/933,527, filed on Sep. 18, 1997, now U.S. Pat. No. 5,789,596.

BROAD DESCRIPTION OF THE INVENTION

1. Field of the Invention

The invention relates to a process for the preparation of 1-acyl-4-arylpiperidines of the general formula:

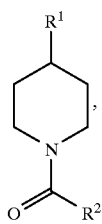

I wherein $R^1$ is an aryl group optionally substituted by one or more $C_{1-6}$-alkyl groups, $C_{1-6}$-alkoxy groups or $C_{1-6}$-alkylthio groups ($C_{1-6}$-alkylsulfanyl groups) or by one or more fluorine atoms, and $R^2$ is a $C_{1-6}$-alkyl group, a $C_{1-6}$-alkoxy group or a benzyloxy group optionally substituted on the phenyl radical by one or more of the aforementioned substituents. It also relates to novel 1-acyl-4-aryl-1, 4-dihydropyridines as intermediates in the process according to the invention.

2. Background Art

The compounds of formula I, in particular those in which $R^2$ forms, with the neighboring carbonyl group, an amino-protective group, such as, benzyloxycarbonyl, are intermediates in the synthesis of neurokinin receptor antagonists (European Published Patent Application No. 0630887; and International Published Patent Application No. WO 95/16682).

Herein, $C_{1-6}$-alkyl groups are in each case taken to mean linear or branched, primary, secondary or tertiary alkyl groups having 1 to 6 carbon atoms, for example, methyl, ethyl, propyl, isopropyl, butyl, isobutyl, sec-butyl, tert-butyl, pentyl, isopentyl, neopentyl, hexyl and so on. Accordingly, $C_{1-6}$-alkoxy groups and $C_{1-6}$-alkylthio groups are taken to mean the ether or thioether groups composed of the aforementioned $C_{1-6}$-alkyl groups and oxygen or sulfur, respectively.

Aryl groups are taken to mean mono-, bi- and polycyclic carbocyclic or heterocyclic aromatic radicals, for example, phenyl, naphthyl, biphenylyl, anthracenyl, furyl, thiophenyl, etc.

In syntheses of compounds of the formula I which are known to date, 1-acyl-4-piperidones are reacted with arylmagnesium halides to give the corresponding 1-acyl-4-aryl-4-hydroxypiperidines. These can either be reduced using triethylsilane directly to give the desired products or be converted into them by elimination of water to give the corresponding 1,2,3,6-tetrahydropyridines and then hydrogenating the resultant double bond. Both processes have the disadvantage that they require an expensive starting material (1-acyl-4-piperidone), and, in addition, the former process also requires an expensive reagent (triethylsilane).

BROAD DESCRIPTION OF THE INVENTION

The main object of the invention is to provide an alternative process which uses less expensive starting materials and is suitable for implementation on an industrial scale.

Other objects and advantages of the invention are set out herein or are obvious herefrom to one skilled in the art.

These objects and advantages of the invention are achieved by the invention process and the novel intermediates of the invention.

It has been found that arylmagnesium halides of the general formula:

II wherein $R^1$ is as defined above and $X^1$ is chlorine, bromine or iodine, can be reacted with the 1-acylpyridinium halides obtainable from pyridine and acyl halides of the general formula:

III wherein $R^2$ is as defined above and $X^2$ is chlorine or bromine, in the presence of a copper compound to give 1-acyl-4-aryl-1,4-dihydropyridines of the general formula:

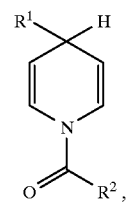

IV wherein $R^1$ and $R^2$ are as defined above, and that the latter can be hydrogenated with homogeneous catalysis to give the desired 1-acyl-4-arylpiperidines.

The aryl group $R^1$ in the arylmagnesium halide II is preferably a phenyl group which may be optionally substituted by one or more $C_{1-6}$-alkyl groups, $C_{1-6}$-alkoxy groups, benzyloxy groups or $C_{1-6}$-alkylthio groups or with one or more fluorine atoms. Particular preference is given to a 2-(methylthio)phenyl group.

The halogen in the arylmagnesium halide II is preferably bromine.

The arylmagnesium halides can be prepared in the usual way from magnesium metal and the corresponding aryl halides. The latter are known compounds and available commercially or can be readily obtained by known processes.

The 1-acyl substituent is preferably the benzyloxycarbonyl group, in which case $R^2$ is a benzyloxy group.

The coreactant of the arylmagnesium halide is the 1-acylpyridinium halide obtainable from the acyl halide III and pyridine, of the general formula:

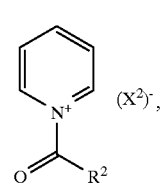

IIIa in which $R^2$ and X are as defined above.

$X^2$ is preferably chlorine.

The 1-acylpyridinium halide IIIa can be prepared either in a one-pot process or in situ, or can alternatively be prepared in a separate step and isolated in pure form. It is also within the scope of the invention to use a 1-acylpyridinium halide IIIa prepared other than by direct reaction of pyridine with the acyl halide III.

Particular preference is given to the embodiments in which the 1-acylpyridinium halide is not isolated, but is formed from acyl halide III and pyridine in a one-pot process or in situ. The pyridine can be, firstly, reacted virtually completely with the acyl halide III to give the 1-acylpyridinium halide IIIa, to which the arylmagnesium halide is then added slowly ("one-pot process"). In another embodiment, the pyridine is introduced initially together with the arylmagnesium halide II and the copper compound, and the acyl halide III is slowly added. The acyl halide reacts initially with the pyridine and the 1-acylpyridinium halide formed in situ immediately reacts with the arylmagnesium halide.

The 1-acylpyridinium halide III is advantageously formed at a temperature of from −80° to +40° C., preferably at −40° to −10° C. The solvent used is expediently an aprotic solvent which does not react with Grignard compounds. Ethers, such as, tetrahydrofuran, are preferably used as the solvent.

The reaction with the arylmagnesium halide II is advantageously carried out under the same conditions as the formation of the 1-acylpyridinium halide III.

The copper compound can be added either prior to the formation of the 1-acylpyridinium halide IIIa or prior to its reaction with the arylmagnesium halide II. Addition of the copper compound affects the regioselective reaction in position 4 of the pyridine ring. Without the addition of copper, a mixture of the products of the addition in position 2 (or 6) and 4 is generally obtained.

The particularly preferred copper compound is copper(I) iodide.

The homogeneous catalysts which are preferably used for the hydrogenation of the 1-acyl-4-aryl-1,4-dihydropyridines IV are platinum metal/phosphine complexes. Examples of suitable platinum metals are ruthenium, rhodium, palladium, iridium and platinum. Particular preference is given to rhodium/phosphine complexes, in particular tris (triphenylphosphine)-rhodium(I) chloride. Surprisingly, 1-acyl-4-aryl-1,4-dihydropyridines having sulfur-containing substituents and O-benzyl groups, such as, 1-benzyloxycarbonyl-4-[2-(methylthio)phenyl]-1,4-dihydropyridine, can also be hydrogenated in this way in good yield without catalyst poisoning or hydrogenolysis of the benzyl group.

The hydrogenation is advantageously carried out at a temperature of from room temperature to 100° C., particularly preferably at 60° to 80° C. The hydrogen pressure is advantageously 1 to 100 bar, with the range from 2 to 50 bar being particularly preferred. Solvents suitable for the hydrogenation are the solvents which are customary for catalytic hydrogenation, for example, low molecular weight alcohols such as methanol or ethanol, esters such as ethyl acetate, or hydrocarbons such as toluene.

Advantageous novel 1-acyl-4-aryl-1,4-dihydropyridines as intermediates of the process according to the invention are the 1-benzyloxycarbonyl-4-aryl-1,4-dihydropyridines of the general formula:

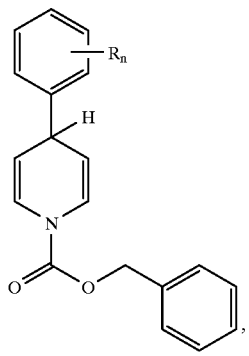

V wherein n is an integer from 0 to 5 and each R radical is chosen, independently of the others, from the group consisting of fluorine, $C_{1-6}$-alkyl, $C_{1-6}$-alkoxy, benzyloxy and $C_{1-6}$-alkylthio.

Particular preference is given to the 1-benzyloxycarbonyl-4-[2-(methylthio)phenyl]-1,4-dihydropyridine of the formula:

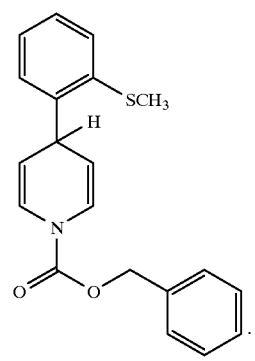

VI

The 1-benzyloxycarbonyl-4-aryl-1,4-dihydropyridines V are preferably prepared by reacting a phenylmagnesium halide of the general formula:

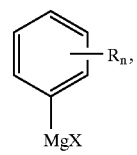

VII wherein X is chlorine, bromine or iodine, and n and R are as defined above, in the presence of copper(I) iodide with 1-benzyloxycarbonylpyridinium chloride formed from pyridine and benzyl chloroformate.

DETAILED DESCRIPTION OF THE INVENTION

The following examples illustrate how the process according to the invention is carried out and the preparation of the compounds according to the invention, but are not to be regarded as a limitation to the invention.

EXAMPLE 1

1-Benzyloxycarbonyl-4-[2-(methylthio)phenyl]-1,4-dihydropyridine

[IV, $R^1$=2-$(CH_3S)C_6H_4$, $R^2$=$OCH_2C_6H_5$]

2.9 g (118 mmol) of magnesium turnings was introduced into 100 ml of tetrahydrofuran (dried over molecular sieve) under argon. Approximately 5 g of 2-bromothioanisole was added dropwise at room temperature, and the mixture was heated to 50° C. After the Grignard reaction had started, the mixture warmed further to reflux. The remainder of the total of 20.0 g (98.5 mmol) of 2-bromothioanisole was added dropwise so that the reaction mixture continued to reflux. The resultant solution of the Grignard compound 2-(methylthio)phenylmagnesium bromide was then allowed to cool slowly to room temperature. Working under argon, 250 ml of dried tetrahydrofuran was introduced into a second flask; 11.7 g (148 mmol) of pyridine and 0.93 g (4.9 mmol) of copper(I) iodide were added; and the mixture was cooled to −30° C. At −30° to −25° C., 16.8 g (98.5 mmol) of benzyl chloroformate was added dropwise, a yellow-red precipitate being formed first, followed by a beige suspension. The solution of the Grignard compound was added dropwise to this suspension at the same temperature; cooling was then stopped and the mixture was stirred for a further 2 hours after it had reached room temperature. The reaction mixture was poured into 120 ml of 20 percent strength aqueous ammonium chloride solution and stirred vigorously. 500 ml of toluene was then added and the phases were separated. The deep blue aqueous phase was extracted three times with 50 ml of toluene each time, and the combined organic phases were dried over sodium sulfate and evaporated to dryness using a rotary evaporator. The brown residue was kept under high vacuum for a further 1 hour to remove solvent residues, then dissolved in 500 to 1000 ml of boiling methanol and filtered while still hot. The filtrate was cooled slowly to room temperature and eventually to +2° C., the product forming as a voluminous yellowish-white precipitate. This was filtered off and dried at 35° C. in vacuo. The yield of the product was 20.8 g (62.7 percent) of yellowish-white solids. Other data concerning the product was:

m.p.: 90.1°–90.9° C.

$^1$H NMR (CDCl$_3$):δ= 2.46(s, 3H); 4.65 (m,1H); 4.95 (br. d, 2H); 5.24 (s, 2H); 6.94 (br. d, 2H); 7.17–7.41 (m, 9H).

$^{13}$C NMR (CDCl$_3$):δ= 16.17; 35.43; 68.21; 108.67; 109.15; 122.49; 122.90; 125.80–129.40 (7 signals); 135.72; 135.79; 143.35; 151.36.

IR (film): 1720.0 cm$^{-1}$ (c=o) 1690.8 (c=c)

MS: m/$_z$= 337 (M$^+$); 322; 292; 278; 247; 246; 214; 202; 186; 155; 115; 91 (100%); 65.

EXAMPLE 2

1-Benxyloxycarbonyl-4-[2-(methylthio)phenyl] piperidine

[I, $R^1$=2-$(CH_3S)C_6H_4$, $R^2$=$OCH_2C_6H_5$]

In an autoclave, 0.137 g (0.148 mmol) of tris-(triphenylphosphine)rhodium(I) chloride was added to a solution of 0.50 g (1.48 mmol) of 1-benzyloxycarbonyl-4-[2-(methylthio)phenyl]-1,4-dihydropyridine (prepared as in Example 1) in 30 ml of degassed absolute ethanol. The mixture was placed under a hydrogen pressure of 45 bar, heated to 70° C. and stirred overnight under these conditions. After the mixture had cooled to room temperature and the hydrogen had been released, the dark brown reaction mixture was filtered through Celite®, and the ethanol was distilled off or a rotary evaporator. The brown oily residue was chromatographed using ethyl acetate/hexane (1:10) or silica gel 60. The yield was 0.386 g (76.3 percent) of colorless oil which partly solidified when left to stand. A sample was purified by crystallizing from a little ethanol in the cold (0° C.) drying at 40° C. in vacuo. Data concerning the product was:

m.p.: 74.9°–75.9° C.

$^1$H NMR (CDCl$_3$): δ= 1.50–1.60 (m, 2H); 1.80–1.90(m, 2H); 2.45 (s, 3H); 2.95 (br. t, 2H); 3.18 (tt, 1H); 4.27 (br. s, 2H); 5.17 (s, 2H); 7.15–7.40 (m, 9H).

$^{13}$C NMR (CDCl$_3$): δ= 16.24; 32.19; 38.81; 44.82; 67.09; 125.50–128.53 (7 signals); 136.72; 137.04; 143.30; 155.40.

MS: m/z= 341 (M$^+$); 296; 250; 206; 177; 135; 91; 56.

What is claimed is:

1. A 1-benzyloxycarbonyl-4-aryl-1,4-dihydropyridine of formula:

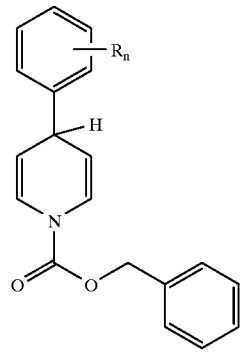

V wherein n is an integer from 0 to 5 and each R radical is chosen, independently of the others, from the group consisting of fluorine, $C_{1\text{-}6}$-alkyl, $C_{1\text{-}6}$-alkoxy, benzyloxy and $C_{1\text{-}6}$-alkylthio.

2. 1-Benzyloxycarbonyl-4-[2-(methylthio)phenyl]-1,4-dihydropyridine of formula:

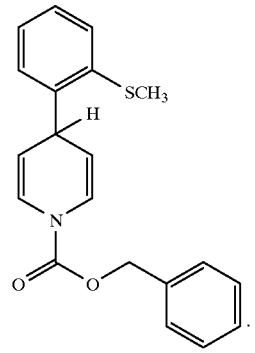

VI

* * * * *